United States Patent

Zaremba et al.

[11] 4,311,664
[45] Jan. 19, 1982

[54] FLAME-PHOTOMETRIC DETECTOR BURNER OF GAS CHROMATOGRAPH

[75] Inventors: Marek Zaremba; Czeslaw Rozycki, both of Warsaw; Rafal Staszewski, Gdansk-Wrzeszcz, all of Poland

[73] Assignee: Wojskowy Instytut Chemii I Radiometrii, Warsaw, Poland

[21] Appl. No.: 895,522

[22] Filed: Apr. 11, 1978

Related U.S. Application Data

[63] Continuation-in-part of Ser. No. 856,163, Nov. 30, 1977, abandoned.

[30] Foreign Application Priority Data

Dec. 8, 1976 [PL] Poland .................................. 194255

[51] Int. Cl.³ .................... G01N 27/62; G01N 31/12
[52] U.S. Cl. .................................... 422/54; 23/232 E; 422/89; 422/91
[58] Field of Search ........... 23/230 PC, 232 E, 232 C, 23/254 E, 253 PC, 254 EF; 422/54, 89, 91

[56] References Cited

U.S. PATENT DOCUMENTS

| | | | |
|---|---|---|---|
| 3,116,979 | 1/1964 | Kapff | 23/230 PC |
| 3,330,960 | 7/1967 | Rich | 23/254 E X |
| 3,399,974 | 9/1968 | Spencer | 23/254 EF |
| 3,607,096 | 9/1971 | Hartmann | 23/232 C X |
| 3,661,533 | 5/1972 | David et al. | 23/232 C X |
| 3,718,430 | 2/1973 | Fischer | 23/232 C X |
| 3,925,023 | 12/1975 | Kaiser | 23/254 EF |

Primary Examiner—Michael S. Marcus
Attorney, Agent, or Firm—Haseltine and Lake

[57] ABSTRACT

A flame-photometric detector burner of a gas chromatograph employing a system of two nozzles arranged in relation to each other for securing mutual flame jump-over from one nozzle onto the other one, and vice versa. One nozzle is designed to supply carrier gas with the substance to be analyzed, and the other is designed to only supply an oxidizer. The outlets of both nozzles are arranged within a hydrogen stream in a cavity of a combustion chamber of a detector block. The nozzle where only the oxidizer is supplied can be electrically insulated from the detector block, and connected to a high-voltage source.

5 Claims, 4 Drawing Figures

FLAME-PHOTOMETRIC DETECTOR BURNER OF GAS CHROMATOGRAPH

BACKGROUND OF THE INVENTION

This is a continuation in-part of application Ser. No. 856,163 filed Nov. 30, 1977 entitled FLAME-PHOTOMETRIC DETECTOR BURNER OF GAS CHROMATOGRAPH now abandoned.

More particularly the present invention relates to a burner of a flame-photometric detector of a gas chromatograph.

Known burners employed in flame-photometric detectors, having combustion occurring in reducing atmosphere, comprise two coaxial nozzles wherethrough gases are supplied to a detector; namely, an inert carrier gas containing the substance to be analyzed, an oxidizer and hydrogen. The burners differ in operation from each other by the method of supplying the gases, more particularly, in the way various combinations of the qualitative compositions of the gases pass through the individual nozzles.

In one type of the burner, the carrier gas containing the substance to be analyzed and the oxidizer are supplied jointly through one nozzle, and hydrogen is provided through the other coaxial nozzle. Designs are known where hydrogen is supplied through the outer nozzle, and the remaining gases are fed through the inner nozzle, and vice versa.

A disadvantage of burners of both types mentioned above, arises in extinguishing the flame in the course of eluting the solvent from the chromatographic column. Extinguishing of the flame can start to occur while injecting onto the chromatographic column liquid samples having a volume of 1 mm$^3$. The first form of the burner of the above-mentioned types is the most advantageous for analytical reasons.

A common feature of other known types of the burners is in separate supplying of the oxidizer through one nozzle, and the carrier gas containing the substance to be analyzed through the other coaxial nozzle, whereby hydrogen is supplied together with the carrier gas or with the oxidizer. In the flow of gases according to the above, a continuity of burning of the flame is attained, but the continuity is also restricted by a certain volume of the liquid sample injected onto the chromatographic column. For instance, in a burner in which the oxidizer flows through the inner nozzle, and carrier gas is fed through the outer nozzle, the flame burns uninterruptedly when samples of a volume not exceeding 10 mm$^3$ are injected. In a burner housing carrier gas through the inner nozzle, and hydrogen mixed with oxidizer through the outer coaxial nozzle, the flame burns uninterruptedly when samples of the volume up to 50 mm$^3$ are injected. This design, however, exhibits the disadvantage that flame-out into the outer nozzle can occur. In order to prevent that, it is necessary to use high flow rates of hydrogen and of the oxidizer. This in turn exhibits the disadvantage that a flame of a large size emits light which significantly increases the background current of the photomultiplier.

In a known gas supply system an oxidizer is provided through the outer nozzle, carrier gas and hydrogen through the inner coaxial nozzle. According to another system, carrier is provided through the outer nozzle, oxidizer and hydrogen through the inner nozzle, and continuity of the burning flame is achieved when the liquid samples of a volume of up to 50 mm$^3$ are injected onto the chromatographic column.

Extinguishing of the flame as a result of the flow of solvent through the burner nozzle gives rise to a disadvantage of the detectors. This is so, since the presence of the flame in the course of eluting the analyzed components of the sample from the column is a necessary condition for proper operation of flame-photometric detectors. Furthermore, the necessary ignition of the flame being extinguished as a result of the flow of the solvent contained in the sample, makes it impossible to maintain the continuity of measurement and to detect analyzed components of the sample eluted from the chromatographic column immediately after the solvent.

The above-described solutions of supplying gases to the detector burner aim to eliminate flame extinguishing, but various combinations of supplying the gases do not eliminate the above disadvantages completely, but only reduce it.

SUMMARY OF THE INVENTION

The main object of the present invention is to overcome the defects of the prior art.

Another object of this invention is to provide a burner design which secures continuity of measurement in the course of injecting liquid samples on a chromatographic column.

The principal features of the invention are directed to a detector burner having a system of two nozzles having their outlets arranged in the stream of hydrogen, situated against each other in a position securing the flame jump-over from one nozzle onto the other and vice versa. One nozzle is connected to the chromatographic column supplying the stream of the carrier gas with the substance to be analyzed to the detector, and to the source of the oxidizer stream, whereas the second nozzle is connected only to the source of the oxidizer stream. The nozzle which is connected only to the source of the oxidizer stream is eventually connected to a high-voltage source and insulated from the other nozzle. In the case when the nozzle is connected to the high-voltage source, it also performs the function of a spark electrode of the flame igniter. The construction of the detector is formed without structure to ignite the flame, such as a discharge electrode or a filament coil. The initiation of the flame by means of a high-voltage spark or a filament does not influence the essence of the design and operation of the burner according to the invention in the course of analysis.

A further feature of the invention employs outlets of the nozzles arranged in close proximity at a distance depending on the respective diameters and on the volume rates of gases flowing therethrough. The inner diameters of the nozzles are chosen depending on employed volume rates of the flowing gases. As a result of such interdependence, the distance between the outlets of the nozzles is determined according to the expected conditions of the analysis.

Other objects and advantages of the present invention will be best understood with respect to the accompanying specification, claims and drawings.

IN THE DRAWINGS

DESCRIPTION OF THE INVENTION

Figure 1:
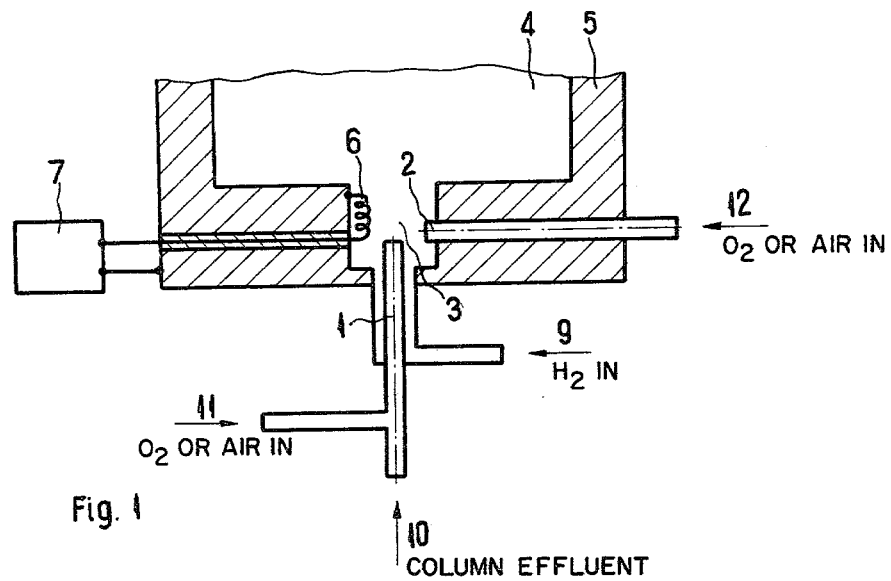
FIG. 1 is a schematic diagram of the detector burner in partial cross-section.

The burner according to the invention as shown in FIG. 1 consists of two nozzles 1 and 2 having outlets arranged within the hydrogen stream 9 in a cavity 3 of the combustion chamber 4 of the detector block 5. Nozzle 1 is where the carrier gas with the substance to be analyzed and the oxidizer are supplied, and nozzle 2 is where only the oxidizer is supplied. The outlets of the nozzles 1 and 2 remain in the immediate vicinity. The axes of the nozzles 1 and 2, lying in a single plane, are situated at the angle of $\pi/2$ and intersect within the zone of cone of the flame burning at the outlet of the nozzle 1. Through the nozzle 1 the stream of the carrier gas 10 containing the substance to be analyzed and the stream of oxidizer 11, and through the nozzle 2 only the stream of the oxidizer 12 are supplied to the chamber 4. A filament 6 is connected to current source 7.

Figure 2:
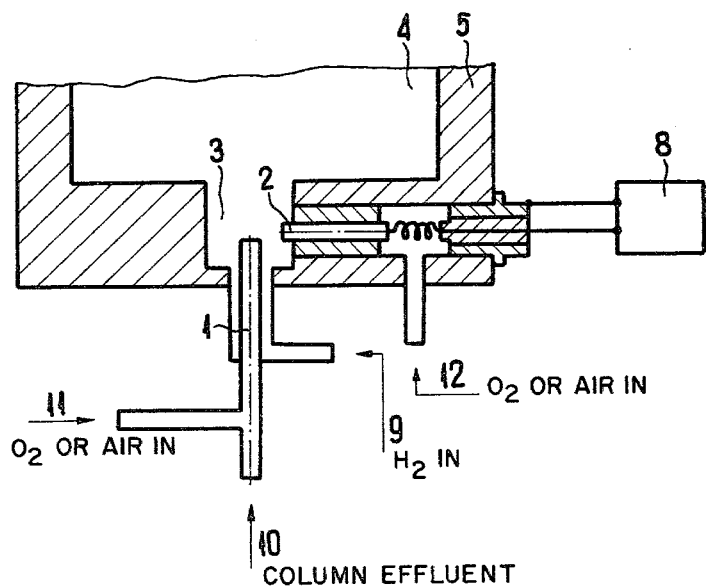
FIG. 2 is another embodiment of FIG. 1.

FIG. 2 illustrates a schematic diagram of a burner according to the invention, in which nozzle 2 is connected to a high-voltage source 8 and is electrically insulated from the detector block 5. The arrangement of the burner within the detector block 5, the arrangement of the nozzles 1 and 2 against each other, as well as the gases supply system are analogous to those shown in FIG. 1.

Before starting the chromatographic analysis of the substance to be examined, the flames are ignited at the outlets of both nozzles in the detector. If the flame is ignited with a high-voltage spark and the nozzle wherethrough only the oxidizer flows performs the function of an electrode, then ignition occurs during the flow of carrier gas and oxidizer through one nozzle. The flow of only oxidizer takes place through the other nozzle, and at a increased flow rate of hydrogen within the stream where the outlets of both nozzles are arranged. Also, the ignition of the flame can occur only at the outlet of the nozzle through which only the oxidizer flows. Then, the ignition of the flame at the outlet of the first nozzle automatically occurs upon turning on carrier gas and the oxidizer through the nozzle. In order to ignite the flames, a high-voltage spark-over is caused between the outlets of both nozzles, or between the oxidizer flow nozzle and the detector block. After igniting the flame at the outlets of both nozzles or at the outlet of the second nozzle only, the volume flow rate of hydrogen can be reduced to the value determined by the conditions of analysis.

Then, measurement is carried out. The sample containing the solvent and the substance to be analyzed is introduced in the stream of carrier gas through a chromatographic column into the combustion chamber, in which the flames burn at the outlets of both nozzles. Liquid samples are evaporated at the inlet of the column. If the volume of the injected liquid sample exceeds 2 mm$^3$, then the solvent vapors cause the flame to extinguish, burning initially at the outlet of the nozzle through which they flow out, but they do not extinguish the flame burning at the outlet of the second nozzle where only the oxidizer flows out. The flame is not extinguished since the diffusion of solvent molecules into the flame is inhibited by the movement of hydrogen molecules, flowing around the outlets of both nozzles.

As a result of such course of analysis, after the solvent is eluted from the chromatographic column, self-ignition of the flame at the outlet of the nozzle where the solvent flowed occurs. This is due to flame jump over from the other nozzle. The analyzed components eluted with the carrier gas are then combusted. The supply of the oxidizer to the second nozzle can now be cut off. The continuity of the measurement is thus ensured and the detector burner according to the invention secures a proper course of the analysis. The flame at the nozzle where the components to be analyzed are eluted is ignited automatically without a necessity as in known designs of the burners to adjust the volume flow rate of hydrogen and of the oxidizer flowing out together with the carrier gas from a common nozzle. The flame jumpover onto the nozzle where the sample to be analyzed is eluted occurs at the moment when the composition of gases flowing out therefrom meets flammability conditions.

Immediately before introduction of the subsequent sample to be examined onto the chromatographic column, the flow of the oxidizer through the other nozzle is turned on; as a result, at its outlets, the flame automatically ignites from the flame burning at the outlet of the first nozzle supplied with the carrier gas and oxidizer. Subsequent measurement is carried out similarly to the former one.

Components of the samples being analyzed, combust in the flame at the outlet of the nozzle, from which they flow, and emit characteristic radiation which is converted to an electric signal which is amplified and recorded in form of a chromatogram.

The analyses can also be carried out with both flames burning, without extinguishing the flame at the outlet of the nozzle where oxidizer only flows. Owing to that or as a result of employing a suitable control system, controlling the time of flow of the oxidizer through the other nozzle makes it possible to employ the burner in fully automated analyzers based upon gas chromatography techniques.

Figure 3A:
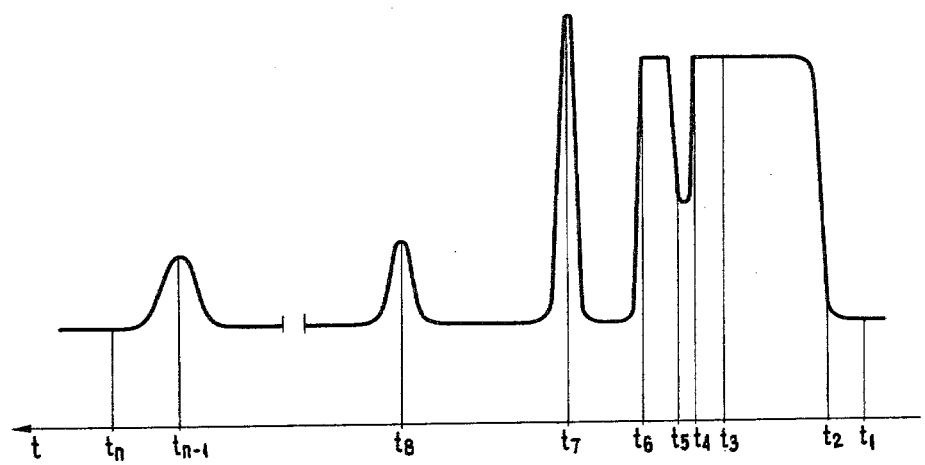
FIG. 3a shows chromatogram obtained in the analysis carried out with application of a burner according to the invention.
Figure 3B:
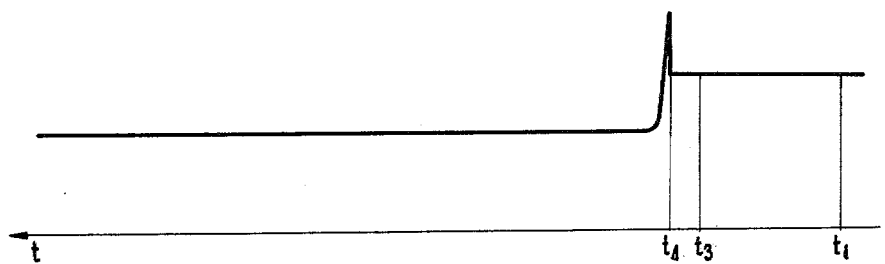
FIG. 3b is another embodiment of FIG. 3a without a nozzle where only an oxidizer is supplied.

The consecutive phases of the course of anaylsis are shown in FIG. 3. FIG. 3a illustrates a chromatogram obtained in the analysis employing a burner according to the invention; whereas, FIG. 3b illustrates another embodiment without a nozzle, where only oxidizer is supplied.

The reference denotations of individual points and sections in FIG. 3 are as follows:

| | |
|---|---|
| $t_1$ | finishing of the previous analysis; |
| $t_2$ | turning on of the flow of the oxidizer through the nozzle 2/self-ignition of the flame at the outlet of nozzle 2 from the flame burning at the outlet of nozzle 1; |
| $t_3$ | introduction of the sample onto the chromatographic column; |
| $t_4$ | extinguishing of the flame burning at the outlet of nozzle 1 by the solvent; |
| $t_5 - t_4$ | elution time of the solvent from the chromatographic column; |
| $t_5'$ | self-ignition of the flame at the outlet of nozzle 1 from the flame burning at the outlet of nozzle 2; |
| $t_6$ | turning off the flow of the oxidizer through the nozzle 2 (extinguishing the flame burning at its outlet); |
| $t_7$ | burning time of the flame at the outlet of nozzle 2; |
| $t_7 - t_3$ | |
| $t_8 - t_3$ | |
| $t_n - 1 - t_3$ | retention times of the consecutive |

| | |
|---|---|
| | analyzed components of the sample introduced onto the chromatographic column; |
| $t_n$ | finishing of the analysis, corresponding with $t_1$ for the subsequent analysis. |

When using a burner not equipped with a nozzle where only the oxidizer is supplied, it is necessary to re-ignite the flame extinguished at time $t_4$. If the time of the flame re-ignition is not shorter than $t_n-t_4$, then in the chromatogram obtained in FIG. 3b, no peaks, representing the components of the sample eluted from the chromatographic column within the time are recorded. During this time the detector is inoperative.

The burner according to the invention possess numerous advantages. Its constructional design permits injection of large volume of samples to be analyzed (over 1000 mm$^3$). It allows detection of components in the analyzed sample, having retention times very similar to the elution time of the solvent. High sensitivity of the detector is achieved since all the molecules of examined components of the sample pass through the flame. The solvent, extinguishing the flame at the outlet of the nozzle from which is flows out, passes through the detector chamber in an unchanged form. Thus, the inside of the detector chamber is not contaminated with the combustion products of the solvent. Moreover, the overload of a photo-multiplier brought about by high intensity of the radiation emitted in the course of combustion of the solvent is eliminated.

Also the advantageous arrangement of the burner nozzles prevents explosions within the detector at the moment of initiation of the flame; since the zones in which the composition of the mixture of oxidizer and hydrogen, corresponding to the composition of the flammable mixture, are localized only at the surrounding of the nozzles outlets, and the remaining portion of the combustion chamber is filled with a mixture of the composition not reaching the threshold of flammability. The above advantage allows construction of a flame-photometric detector of increased volume of the combustion chamber.

An additional advantage of the design according to the invention is the utilization of the nozzle, where only oxidizer is supplied, as a spark electrode for flame ignition. Thus, from the space viewed by the photo-multiplier, foreign members, such as a discharge electrode or a filament coil, are eliminated.

Many modifications and variations of the present invention are possible in light of the above teachings. It is, therefore, to be understood that within the scope of the appended claims, the invention may be practiced otherwise than as particularly described.

What we claim is:

1. A flame photometric detector in combination with a flame photometric detector burner and a gas chromatrographic column, said detector having a housing including a combustion chamber, said housing allowing maintenance of a hydrogen atmosphere inside the chamber and having detection means for measuring electromagnetic radiation emitted during analysis of components from said chromatographic column, said flame photometric detector burner comprising: a housing with bottom and side walls, cavity means defined in said bottom wall, flame ignition means within said cavity means, first and second nozzle means connected to said housing and communicating with the interior of said cavity means, said first and second nozzle means being disposed with respective axes in a single plane and each nozzle means terminating upstream of the downstream end of said cavity means, said first nozzle means extending through said bottom wall of said housing and being spaced from a vertical wall of said cavity means to form an annular space, said second nozzle means extending through said vertical wall of said cavity means and having its outlet end terminating just downstream of the outlet end of said first nozzle means without intersecting the vertical axis of said first nozzle means, hydrogen gas inlet means surrounding said first inlet means, means for supplying hydrogen gas to said hydrogen inlet means to form a hydrogen atmosphere in said cavity said nozzle means being positioned to secure mutual flame jump over from one nozzle to another and vice versa, means for supplying a gas containing oxygen to each of said nozzle means, and said chromatographic column having means for supplying a sample from said chromatographic column, via a carrier gas, to said first nozzle means.

2. A flame photometric detector burner of a gas chromatograph as in claim 1, wherein: means defining a high voltage source are connected to said second nozzle means, said second nozzle means are electrically insulated from said housing walls and additionally functions as said ignition means.

3. A flame photometric detector burner of a gas chromatograph as in claim 1, wherein: said ignition means comprises a discharge electrode.

4. A flame photometric detector burner of a gas chromatograph as in claim 1, wherein: said ignition means comprises a filament coil.

5. A flame photometric detector burner of a gas chromatograph as in claim 1, wherein: said respective axes of said nozzle means lie in a common plane and are at an angle of $\pi/2$ rad.

* * * * *